US006838279B2

(12) United States Patent
Wechsler et al.

(10) Patent No.: US 6,838,279 B2
(45) Date of Patent: Jan. 4, 2005

(54) HERPES SIMPLEX VIRUS TYPE 1 (HSV-1)-DERIVED VECTOR FOR SELECTIVELY INHIBITING MALIGNANT CELLS AND FOR EXPRESSING DESIRED TRAITS IN MALIGNANT AND NON-MALIGNANT MAMMALIAN CELLS

(75) Inventors: Steven L. Wechsler, Westlake Village, CA (US); Anthony B. Nesburn, Malibu, CA (US); Guey-Chuen Perng, Alhambra, CA (US); John S. Yu, Los Angeles, CA (US); Keith L. Black, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 167 days.

(21) Appl. No.: 10/046,491

(22) Filed: Oct. 29, 2001

(65) Prior Publication Data

US 2002/0098170 A1 Jul. 25, 2002

Related U.S. Application Data

(62) Division of application No. 09/299,817, filed on Apr. 26, 1999, now Pat. No. 6,774,119.

(51) Int. Cl.⁷ .................. A61K 48/00; C12N 15/63; C12N 15/87; C12N 5/00

(52) U.S. Cl. .................. 435/320.1; 435/325; 435/455; 435/456; 435/69.1; 514/44; 424/199.1

(58) Field of Search .................. 435/320.1, 325, 435/455, 456, 69.1; 514/44; 424/199.1

(56) References Cited

U.S. PATENT DOCUMENTS

| | | | |
|---|---|---|---|
| 4,769,331 A | 9/1988 | Roizman et al. | |
| 4,859,587 A | 8/1989 | Roizman | |
| 5,112,596 A | 5/1992 | Malfroy-Camine | |
| 5,268,164 A | 12/1993 | Kozarich et al. | |
| 5,288,641 A | 2/1994 | Roizman | |
| 5,328,688 A | 7/1994 | Roizman | |
| 5,434,137 A | 7/1995 | Black | |
| 5,527,778 A | 6/1996 | Black | |
| 5,585,096 A | 12/1996 | Martuza et al. | |
| 5,599,691 A | 2/1997 | Roizman | |
| 5,670,477 A | 9/1997 | Poduslo et al. | |
| 5,728,379 A | 3/1998 | Martuza et al. | |
| 6,193,980 B1 * | 2/2001 | Efstathiou | 424/199.1 |
| 6,340,673 B1 * | 1/2002 | Roizman | 514/44 |

FOREIGN PATENT DOCUMENTS

| WO | WO 92/13943 | 8/1992 |
|---|---|---|
| WO | WO 98/04726 * | 2/1998 |

OTHER PUBLICATIONS

Ho et al. (1996) Mol. Brain Res., vol. 41 (1–2), 200–209.*

Huard, J. et al., *Herpes simplex virus type 1 vector–mediated gene transfer to muscle*, Gene Ther. 2(6):385–92 [Aug. 1995], Abstract only.

Barnettm F. H., Selective delivery of herpes virus vectors to experimental brain tumors using RMP–7, Cancer Gene ther, 6(1):14–20 (Jan.–Feb. 1999). Abstract Only.

Bi, Wan Li et al., "In Vitro Evidence that Metabolic Cooperation is Responsible for the Bystander Effect Observed with HSV tk Retroviral Gene Therapy," Human Gene Therapy, 4:725–731 (1993).

Bovintsis, E. J. et al., "Long–term survival of rats barb ring brain neoplasms treated with gancici vir and a herpes simplex virus vector that retains an intact thymidine kinase gene," Cancer Res, 54(22):5745–51, (N v 15, 1994). Abstract Only.

Culver, Kenneth W., "Clinical Applications of Gene Therapy for Cancer," Clinical Chemistry, vol. 40, N90. 4, pp. 510–512, (1994).

Doran, S. E. et al., "Gene expression from recombinant viral vectors in the central nervous system after blood–brain barrier disruption," Neurosurgery, 36(5):965–70, (May 1995). Abstract Only.

Kramm, C. M. et al., "Herpes vector–mediated delivery of marker genes to disseminated central nervous system tum rs," Hum Gene Ther, 7(3):291–300, (Feb 10, 1996). Abstract Only.

Kramm, C. M. et al., "Therapeutic efficiency and safety of a second–generation replication–conditional HSV1 vector for brain tumor gene therapy," Hum Gene Ther, 8(17):2057–68, (Nov. 20, 1997). Abstract Only.

Kroll, R. A. et al., Improving drug delivery to intracerebral tumor and surrounding brain in a rodent model: a comparison of osmotic versus bradykinin modification of the blood–brain and/or blood–tumor barriers, Neurosurgery, 43(4):879–86; discussion 886–9, (Oct. 1998). Abstract Only.

(List continued on next page.)

*Primary Examiner*—Anne Marie S. Wehbé
(74) *Attorney, Agent, or Firm*—Pillsbury Winthrop LLP

(57) ABSTRACT

Disclosed is an HSV-1-derived vector containing a DNA having a functional LAT promoter, or operative fragment thereof, a deletion in both copies of the HSV-1 LAT gene, and a deletion in both copies of the HSV-1 ICP34.5 gene. The HSV-1-derived vectors are non-neurovirulent and do not spontaneously reactivate from latency, and they optionally contain a functional HSV thymidine kinase gene, which can enhance the effectiveness against cancer of drug treatment with gancyclovir or acyclovir. Alternatively, the HSV-1-derived vectors contain at least one transcriptional unit of a LAT promoter sequence operatively linked to a nucleic acid encoding a preselected protein. In some embodiments, the preselected protein is a nucleotide sequence encoding a polypeptide toxic for cells expressing the vector, for example, human interferon-γ. Also, disclosed are kits for expressing in a mammalian cell a gene encoding a preselected protein, and mammalian cells containing the HSV-derived vectors.

4 Claims, 9 Drawing Sheets

OTHER PUBLICATIONS

Markert, James M. et al., "Expanded spectrum of viral therapy int he treatment of nervous system tumors," J. Neurosurg, 77:590–594 (1992).

Markert, James M. et al., "Reduction and Elimination of Encephalitis in an Experimental Glloma Therapy Model with Attenuated Herpes Simplex Mutants that Retain Susceptibility to Acyclovir," Neurosurgery, vol. 32, No. 4, pp. 597–603, (Apr. 1993).

Martuza, Robert L., "Experimental Therapy of Human Gllomo by Means of a Genetically Engineered Virus Mutant," Science, vol. 252, pp. 854–856 (May 10, 1991).

Mineta, Toshihiro et al., "Mutant Viral Therapy for Malignant Brain Tumors Using Ribonucleotide Reductase–Deficient Herpes Simplex Virus 1," J. Neurosurg., vol. 80, No. 2, p. 381 (Feb. 10, 1994). Meeting Program Item #1534.

Moore, Alice E., "Effects of Viruses on Tumors," Annual Review of Microbiology, vol. 8, pp. 393–410 (1954).

Moore, A. E., "The Oncolytic Viruses," Experimental Tumor Research/Sloan–Kettering Institute for Cancer Research, 1:411–439, (1960).

Muldoon, L. L. et al., "Comparison f intercerebral inoculation and smotic blood–brain barrier disruption for delivery of adenovirus, herpesvirus, and iron oxide particles to normal rat brain," Am J Pathol, 147(6):1840–51 (Dec. 1995). Abstract Only.

Nilaver,G. et al., "Delivery of herpesvirus and adenovirus to nude rat intracerebral tumors after osmotic blood–brain barrier disruption," Proc Natl Acad Sci U S A, 92(21):9829–33 (Oct. 10, 1995). Abstract Only.

Muldoon, L. L. et al., "A physiological barrier distal to the anatomic blood–brain barrier in a model of transvascular delivery," AJNR Am J Neuroradiol, 20(2):217–22 (Feb. 1999). Abstract Only.

Neuwelt, E. A. et al., "Delivery of ultraviolet–inactivated 35S–herpesvirus across an osmotically modified blood–brain barrier," J Neurosurg, 74(3):475–9 (Mar. 1991). Abstract Only.

Neuwelt, E. A. et al., "Delivery of virus–sized iron oxide particles to rodent CNS neurons," Neurosurgery, 34(4):777–84 (Apr. 1994). Abstract Only.

Oldfield, Edward H. et al., Clinical Protocols, Gene Therapy for the Treatment of Brain Tumors Using Intra–Tumoral Transduction with Thymidine Kinase Gene and Intravenous Ganciclovir, Human Gene Therapy, 4:39–69 (1993).

Perng, G. C. et al.., "Evidence that the HSV–1 LAT's Main Role May be in Reactivation from Latency Rather than in Establishment of Latency," Abstract presented at Association for Research in Vision and Opthalmology (ARVO) May 1997.

Perng, Guey–Chuen et al, "The Latency–Associated Transcript Gene of Herpes Simplex virus Type 1 (HSV–1) is Required for Efficient In Vivo Spontaneous Reactivation of HSV–1 from Latency," Journal of Virology, vol. 68, No. 12, pp. 8045–8055 (Dec. 1994).

Perng, Guey–Chuen et al., " An Avirulent ICP34.5 Deletion Mutant of Herpes Simplex virus Type 1 is Capable of In Vivo Spontaneous Reactivation," Journal of Virology, vol. 60, No. 5, pp. 3033–3041 (May 1995).

Perng, Guey–Chuen et al., "High–Dose Oscular Infection with a Herpes Simplex Virus Type 1 ICP 34.5 Deletion Mutant Produces No Corneal Disease or Neurovirulence yet Results in Wild–Type Levels of Spontaneous Reactivation," Journal of Virology, vol. 70, No. 5, pp. 2883–2893 (May 1996).

Rainov, N. G. et al. "Long–term survival in a rodent brain tumor model by bradykinin–enhanced intra–arterial delivery f a therapeutic herpes simplex virus vector," Cancer Gene Ther, 5(3):158–62 (May–Jun. 1998). Abstract Only.

Rainov, N. G. et al. "Intraarterial delivery of adenovirus vectors and liposome–DNA complexes to experimental brain neoplasms," Hum Gene Ther, 10(2):311–8 (Jan. 20, 1999). Abstract Only.

Rainov, N. G. et al., "A chimeric fusion protein f cytochrome CYP4B1 and green fluorescent protein for detection of pro–drug activating gene delivery and for gene therapy in malignant glloma," Adv Exp Med Biol, 451:393–403 (1998). Abstract Only.

Rapoport, S. I., et al., "Tight–junctional modification as the basis of osmotic opening of the blood–brain barrier," Ann N Y Acad Sci, 481:250–67 (1986). Abstract Only.

Yang, W. et al., "Enhanced delivery of boronophenylkalanine for neutron capture therapy by means of intracarotid injection and blood–brain barrier disruption," Neurosurgery, 38(5):985–92 (May 1996), Abstract Only.

Rainov, N. G. et al., "Selective uptake of viral and monocrystalline particles delivered intra–arterially to experimental brain neoplasms," 6(12):1543–52 (Dec. 1995). Abstract Only.

Anderson, W. F., *Gene therapy scores against cancer*, Nat. Med. 6(8):862–63 [Aug. 2000].

Delman, K.A. et al., *Effects of pre–existing immunity on the response to herpes simplex–based oncolytic viral therapy*, Human Gene Therapy 11:2465–72 [2000].

Ebbinghaus, C. et al., *Functional and selective targeting of adenovirus to high–affinity Fcy receptor 1–positive cells by using a bispecific hybrid adapter*, J. Virol. 75(1):480–489 [2001].

Haisma, H.J. et al., *Targeting of adenoviral vectors through a bispecific single–chain antibody*, Cancer Gene Ther. 7(6):901–04 [2000], Abstract Only.

Markert, J.M. et al., *Conditionally replicating herpes simplex virus mutant, G207 for the treatment of malignant glioma: results of a phase 1 trial*, Gene Therapy 7:867–74 [2000].

Miller, C.R. et al., *Differential susceptibility of primary and established human cells to adenovirus infection: targeting via the epidermal growth factor receptor achieves fiber receptor–independent gen transfer*, Cancer Res. 58:5738–5748 [1998].

Mullen, C.A. et al., *Molecular analysis of Tlymphocyte–directed gene therapy for adenosine deaminase deficiency: long–term expression in vivo of genes intorduced with a retroviral vector*, Human Gene Therapy 7:1123–1129 [Jun. 1996].

Nesburn, A.B. et al., *Therapeutic periocular vaccination with subunit vaccine induces higher levels of herpes simplex virus–specific tear secretory immunoglobulin A than systemic vaccination and provides protection against recurrent spontaneous ocular shedding of virus in latently infected rabbits*, Virology 252:200–09 [1998].

Oyama, M et al., *Oncolytic viral therapy for human prostate cancer by conditionally replicating herpes simplex virus 1 vector G207*, Jpn. J. Cancer Res. 91(12):1339–44 [2000a], Abstract only.

Oyama, M. et al., *Intravesical and intravenous therapy of human bladder cancer by the herpes vector G207*, Hum. Gene Ther. 11(12):1683–93 [2000b], Abstract only.

Porada et al., *In utero gene therapy: transfer and long–term expression of the bacterial neor gene in sheep after direct injection of retroviral vectors into preimmune fetuses*, Human Gene Therapy 9:1571–85 [Jul. 20, 1998].

Toda, M. et al., *Herpes simplex virus as an in situ cancer vaccine for the induction of specific anti–tumor immunity*, Hum. Gene Ther. 10(3):385–93 [1999], Abstract only.

Walker, J.R. et al., Local and systemic therapy of human prostate adenocarcinoma with the conditionally replicating herpes simplex virus vector G207, Hum. Gene Ther. 10(13):2237–43 [1999], Abstract only.

International Search Report, PCT/US 00/11031, mailed Sept. 4, 2000.

McGeoch, Duncan J., et al., *Comparative sequence analysis of the long repeat regions and adjoining parts of the long unique regions in the genomes of herpes simplex viruses types 1 and 2, Journal of General Virology*, vol. 72: pp. 3057–3075 (1991).

Kramm, Christof M., et al., *Gene Therapy for Brain Tumors, Brain Pathology*, vol. 5: pp. 345–381 (1995).

* cited by examiner

HERPES SIMPLEX VIRUS TYPE 1 (HSV-1)-DERIVED VECTOR FOR SELECTIVELY INHIBITING MALIGNANT CELLS AND FOR EXPRESSING DESIRED TRAITS IN MALIGNANT AND NON-MALIGNANT MAMMALIAN CELLS

This application is a division of U.S. Ser. No. 09/299,817, filed on Apr. 26, 1999, now U.S. Pat. No. 6,774,119.

The U.S. Government has a paid-up license in this invention and the right in limited circumstances to require the patent owner to license others on reasonable terms as provided for by the terms of grants EY07566 and EY10243 awarded by the NIH Public Health Service.

BACKGROUND OF THE INVENTION

Throughout this application various publications are referenced within parentheses. The disclosures of these publications in their entireties are hereby incorporated by reference in this application in order to more fully describe the state of the art to which this invention pertains.

1. Field of the Invention

The present invention is related to the medical arts, particularly to the field of gene therapy.

2. Discussion of the Related Art

Viruses have been tested for their ability to treat various types of malignancies in animals and humans. The proposed therapeutic mechanisms of viral tumor therapy in the prior art include: (i) producing new antigens on the tumor cell surface to induce immunologic rejection, called "xenogenization," and (ii) direct killing of the tumor cell by a virus, called "oncolysis."

Several animal models and animal types of malignant tumor have been used to study oncolysis with wild-type viruses. (Moore, *Ann. Rev. Microbiol.* 8: 393 [1954]; Moore, *Progr. Exp. Tumor Res.* 1: 411 [1960]). At least nine viruses have been shown to be capable of inducing some degree of tumor regression of a variety of tumors in animals. A major drawback found in these early studies, however, was systemic infection of the patient by the virus.

Later in the quest for a viral therapy for cancer, clinical trials employing herpes viral vector therapy were approved in the United States to treat human tumors. (Culver, *Clin. Chem.* 40: 510 [1994]). These studies employed replication-incompetent or defective viruses to potentially overcome the problem of systemic infection by the virus. However, the use of replication-defective herpes viruses for treating malignant tumors requires producer cells because each replication-defective herpes virus particle can enter only a single cell and cannot productively infect others thereafter. Thus, due to their inability to replicate, replication-defective herpes viruses cannot spread to other tumor cells, they are unable to penetrate a deep, multilayered tumor in vivo. (Markert et al., *Neurosurg.* 77: 590 [1992]).

On the other hand, the herpes simplex virus type 1 (HSV-1) appears to be particularly well suited for use in the treatment of malignancies. Mutation of several of the viral genes involved in DNA replication, including UTPase and thymidine kinase- render the virus replication-defective in normal postmitotic cells, like neurons, but replication-competent in dividing cells, which can complement the defect. In addition, the HSV-thymidine kinase (TK) gene product can convert the anti-herpes drugs gancyclovir or acyclovir to nucleotide analogs which block both viral and cellular replication, thereby killing dividing tumor cells.

The need for a safe and effective HSV-1-derived vector is especially acute with respect to malignant tumors of the central nervous system. These malignancies are usually fatal, despite recent advances in the areas of neurosurgical techniques, chemotherapy and radiotherapy. In particular, there are no standard therapeutic modalities that can substantially alter the prognosis for patients with malignant tumors of the brain, cranium, and spinal cord. For example, high mortality rates persist for patients diagnosed with malignant medulloblastomas, malignant meningiomas, malignant neurofibrosarcomas and malignant gliomas, which are characterized by infiltrative tumor cells throughout the brain. Although intracranial tumor masses can be debulked surgically, treated with palliative radiation therapy and chemotherapy, the survival associated with a diagnosis of glioma, especially glioblastoma, is typically measured in months.

Oldfield et al. introduced viral vectors carrying the herpes simplex virus (HSV)-1 thymidine kinase (HS-tk) gene into brain tumor cells in human patients. (Oldfield et al., *Human Gene Therapy* 4: 39 [1993]). In this study, there was some evidence of anti-tumor effect in five of the eight patients in the clinical trial. However, none of the patients was cured of brain cancer. Some of the limitations of current viral based therapies, described by Oldfield, include: (1) the low titer of virus produced; (2) virus spread limited to the region surrounding the producer cell implant; (3) possible immune response to the producer cell line; (4) possible insertional mutagenesis and transformation of virally infected cells; (5) a single treatment regimen of the drug, gancyclovir, because the "suicide" product kills virally infected cells and producer cells; and (6) the bystander effect of killing being limited to cells in direct contact with the virally transformed cells. (Bi, W. L. et al., *Human Gene Therapy* 4: 725 [1993]).

During the early 1990's, the use of genetically engineered replication-competent HSV-1 viral vectors was first explored in the context of finding an antitumor viral therapy. Replication-competent mutants of herpes simplex virus type I (HSV-1) with single mutations demonstrated therapeutic potential against experimental malignant brain tumors, while being attenuated for neurovirulence. It was thought that a replication-competent virus would have the advantage of being able to enter one tumor cell, make multiple copies of its genome, lyse the cell and spread to other tumor cells. A thymidine kinase-deficient (TK$^-$) mutant, dlsptk, was able to destroy human malignant glioma cells implanted into the brain of an animal. (Martuza et al., *Science* 252: 854 [1991]). The major disadvantage to this system was that these TK$^-$ mutants were only moderately attenuated for neurovirulence, i.e., the ability to replicate in brain cells causing inflammation of the brain, and they produced encephalitis at the doses required to kill the tumor cells adequately. (J. M. Markert et al., *Neurosurgery* 32: 597 [1993]). Roizman described a HSV-based TK$^-$ vector system capable of expressing foreign genes inserted into the TK gene. (Roizman, Herpes Simplex Virus as a Vector, U.S. Pat. Nos. 5,599,691 and 5,288,641). Residual neurovirulence of TK$^-$ limits the usefulness of such vectors for tumor therapy.

Other single mutants of HSV-1 included hrR3, containing an insertion of the *Escherichia coli* lacZ gene into the viral ICP6 gene, which encodes the ribonucleotide reductase large subunit (T. Mineta et al., Gene Therapy 1:S78 [1994]; T. Mineta et al., *J. Neurosurg.* 80:381 [1994]) and R3616 containing deletions in both copies of the γ34.5 gene, a neurovirulence gene. (Markert et al., *Neurosurgery* 32:597 [1993]). Roizman described a recombinant, purportedly avirulent HSV lacking the ability to express a functional γ34.5 gene product, a neurovirulence factor. (Roizman, Recombinant Herpes Simplex Viruses vaccines and methods, U.S. Pat. No. 5,328,688). Spontaneous reactivation rates of these mutants was only relatively attenuated, not entirely eliminated. (E.g., G.-C. Perng et al., J. Virol. 70(5):2883–93 [1996]; G.-C. Perng et al., J. Virol. 69(5):3033–411 [1995]).

Multi-mutated HSV-1 mutants have been described having augmented safety. Multiple mutations engineered into HSV-1 made the possibility of reversions of wild type unlikely and confirmed multiple and potentially synergistic safety features by attenuating of multiple mechanisms of virulence. Kranm et al. reported a HSV-1 mutant vector, MGH-1, defective for both ribonucleotide reductase and γ34.5, which had higher therapeutic safety than hrR3, but had clearly decreased therapeutic efficiency compared to hrR3. (C. M. Kramm et al., *Therapeutic efficiency and safety of a second-generation replication-conditional HSV1 vector for brain tumor gene therapy*, Hum. Gene Ther. 8(17):2057–68 [1997]). Martuza et al. taught a replication competent HSV-1 vector having deletions in both of its γ34.5 genes, as well as in the ICP6 gene which encodes for the large sub unit of the HSV ribonucleotide reductase. (Martuza et al., Replication-competent Herpes Simplex Virus mediates destruction of neoplastic cells, U.S. Pat. No. 5,585,096). Martuza et al. taught a HSV-1-derived replication competent vector for tumor therapy that was driven by a tumor-specific or cell-specific promoter and was purportedly not neurovirulent. (Martuza et al., Tumor- or cell-specific Herpes Simplex Virus replication, U.S. Pat. No. 5,728,379). Although improved in safety, these mutants have shown attenuated therapeutic potential.

Even while some of these mutants, for example, γ34.5 mutants, have been shown to reduce neurovirulence by as much as 100,000 fold in mice, a major problem with existing technology is the spontaneous reactivation of HSV-1. Following infection at a peripheral site, HSV-1 establishes a life long latent infection of the sensory neurons enervating the peripheral site. In the absence of viral reactivation, latency is totally benign, with no known pathology. In rabbits, which can have rates of spontaneous HSV-1 reactivation comparable to those seen in humans, HSV-1 γ34.5 mutants have greatly reduced spontaneous reactivation when rabbits are infected at "normal" doses ($2 \times 10^5$ pfu/eye). (G.-C. Perng et al., *An Avirulent ICP34.5 deletion mutant of Herpes Simplex Virus Type 1 is capable of in vivo spontaneous reactivation*, J. Virol. 69(5):3033–41 [1995]). In contrast, at extremely high infectious doses ($2 \times 10^8$ pfu/eye) wild type spontaneous reactivation rates are achieved, separably from level of neurovirulence. (G. C. Perng et al., *High-dose ocular infection with a Herpes Simplex Virus Type 1 ICP34.5 deletion mutant produces no corneal disease or neurovirulence yet results in wild-type levels of spontaneous reactivation*, J. Virol. 70(5):2883–93 [1996]).

During neuronal latency, latency-associated transcript (LAT) is the only viral gene that is abundantly transcribed. This is a function of the LAT promoter, a very powerful promoter with significant neuronal specificity. LAT is essential for efficient spontaneous reactivation. In rabbits, HSV-1 LAT null mutants have spontaneous reactivation rates of ⅓ or less than that of wild type or rescued viruses. (G. C. Perng et al., *The Latency-Associated Transcript gene of Herpes Simplex Virus Type 1 (HSV-1) is required for efficient in vivo spontaneous reactivation of HSV-1 from latency*, J. Virol. 68(12):8045–55 [1994]). But this is still a substantial level of spontaneous reactivation.

Therefore, there is a desideratum for an effective HSV vector for brain tumor therapy that is non-neurovirulent and also does not reactivate spontaneously.

Delivery of the virus particles to tumor cells is another problem encountered in HSV therapy against brain tumors. Stereotactic inoculation of virus particles directly into a brain tumor has commonly been limited to small tumors, because the small volume of distribution by stereotactic inoculation limits the efficacy of viral therapy for large and disseminated tumors. (L. L. Muldoon et al., *Comparison of intracerebral inoculation and osmotic blood-brain disruption for delivery of adenovirus, herpesvirus, and iron oxide particles to normal rat brain*, Am. J. Pathol. 147(6):1840–51 [1995]).

Kramm et al. described intrathecal injection of HSV vector hrR3 into the cerebrospinal fluid of rats with gliosarcomas, which resulted in HSV expression in frontal tumors and leptomeningeal tumor foci along the entire neuroaxis; however there was substantial toxicity associated with intrathecal injection of the vector. (C. M. Kramm et al., *Herpes vector-mediated delivery of marker genes to disseminated central nervous system tumors*, Hum. Gene Ther. 7(3):291–300 [1996]).

Transvascular delivery of viral particles to tumor cells is hampered by the blood-brain barrier, and particularly the blood-tumor barrier, that results from the interendothelial tight junctions formed by cerebrovascular endothelial cells.

Neuwelt et al. used an intracarotid injection of hypertonic mannitol to osmotically disrupt the blood-brain barrier. They reported that this enhanced the uptake by brain tissue of inactivated HSV-1 particles that were administered immediately afterward by bolus intracarotid injection, but there was no such enhancement when HSV was injected intravenously. (E. A. Neuwelt et al., *Delivery of ultraviolet-inactivated 35S-herpesvirus across an osmotically modified blood-brain barrier*, J. Neurosurg. 74(3):475–79 [1991]; Also, S. E. Doran et al., *Gene expression from recombinant viral vectors in the central nervous system after blood-brain barrier disruption*, Neurosurgery 36(5):965–70 [1995]; G. Nilaver et al., *Delivery of herpesvirus and adenovirus to nude rat intracerebral tumors after osmotic blood-brain barrier disruption*, Proc. Natl. Acad. Sci. USA 92(21):9829–33 [1995]).

Rainov et al. described enhanced transvascular delivery of HSV into gliosarcoma cells in the brains of rats by injecting bradykinin, a vasoactive polypeptide, into the internal carotid artery to disrupt the blood-brain barrier. (N. G. Rainov, *Selective uptake of viral and monocrystalline particles delivered intra-arterially to experimental brain neoplasms*, Hum. Gene. Ther. 6(12):1543–52 [1995]; N. G. Rainov et al., *Long-term survival in a rodent brain tumor model by bradykinin-enhanced intra-arterial delivery of a therapeutic herpes simplex virus vector*, Cancer Gene Ther. 5(3):158–62 [1998]). A bradykinin analog, RMP-7, was shown to selectively open the blood-tumor barrier in rats to hrR3 HSV particles without the hypotensive effects associated with the use of bradykinin. (F. H. Barnett et al., *Selective delivery of herpes virus vectors to experimental brain tumors using RMP-7*, Cancer Gene Ther. 6(1):14–20 [1999]).

There is a definite need for an effective HSV-1-derived vector for cancer therapy, that is virulence impaired and also does not reactivate spontaneously. There is a further definite need for a method of inhibiting malignant cells using such an HSV-1-derived vector that is also capable of reaching tumors of the central nervous system, particularly brain tumors. These and other benefits the present invention provides as described herein.

SUMMARY OF THE INVENTION

The present invention is directed to a method of selectively inhibiting the growth of malignant cells in mammals, including humans. The method selectively inhibits the growth of malignant cells of all varieties, and is particularly useful in treating brain tumors and other malignancies of the central nervous system. The method employs an HSV-1-derived viral vector containing a deletion in both copies of the LAT gene and both copies of the ICP34.5 gene of HSV-1, and which is delivered to the malignant cell. One of the advantages of using a combined LAT null and γ34.5 null HSV-1-derived vector, compared to LAT null mutants or γ34.5 null mutants alone, is that regardless of the infectious dose, the double mutant does not reactivate from latency. The HSV-1-derived vector of the present invention employed in the method, optionally contains a functional HSV thymidine kinase gene, which can enhance the effectiveness against cancer of drug treatment with gancyclovir or acyclovir.

The combination of LAT null and γ34.5 null mutations results in a viral vector that does not damage neurons, but grows well and kills most other cells. Alternatively, the method employs an HSV-1-derived vector that contains at least one transcriptional unit of a LAT promoter sequence operatively linked to a nucleic acid having a nucleotide sequence encoding a polypeptide toxic for cells expressing the vector, for example, human interferon-γ, interleukin-2, interleukin-4, interleukin-6, interleukin-10, interleukin-12, granulocyte-macrophage colony stimulating factor, tumor necrosis factor-α, Fas ligand, human connexin-43, VP-16, or VP-22.

The present invention relates to a method of expressing a preselected protein in a mammalian cell, employing a vector of the present invention that contains at least one transcriptional unit of a constitutive LAT promoter operatively linked to a gene encoding any preselected protein. When the infected cell expresses, from the LAT promoter, it produces the preselected protein in an elevated amount compared to uninfected homologous cells. Thus, the present invention also relates to a method of treating a genetic defect in a mammal that is based on expressing a desired preselected protein, using a vector in accordance with the present invention, to mitigate or ameliorate a genetic disease condition.

The present invention also relates to a method of detecting a mammalian cell that expresses HSV, employing an HSV-1-derived vector, with the same double deletion of LAT and ICP34.5 genes, and a fluorescent or light-emitting (green fluorescent protein) gene inserted into the vector under the transcriptional control of the LAT promoter. The resulting fluorescence or luminescence allows easy detection of the location of the HSV-1 expressing cell, when tissue sections are examined under a fluorescent microscope or when cells are analyzed with flow-activated cell sorting (FACS).

The present invention is also directed to HSV-1-derived vectors and kits for expressing a preselected protein in a mammalian cell, useful for practicing the method, and to mammalian cells containing the HSV-derived vectors.

These and other advantages and features of the present invention will be described more fully in a detailed description of the preferred embodiments which follows.

DETAILED DESCRIPTION OF THE PREFERRED EMBODIMENTS

The present invention is directed to a method of selectively inhibiting the growth of malignant cells in mammals, including humans, non-human primates, for example simians, rodents such as mice and rats, gerbils, hamsters, and rabbits. The method selectively inhibits the growth of malignant cells of all varieties, compared to the effect on non-malignant cells, in malignant tumors in any body tissue or cavity, including malignant tumors in the brain, spine, skull, thorax, lung, peritoneum, prostate, ovary, uterus, breast, stomach, liver, bowel, colon, rectum, bone, lymphatic system, and skin. The method is useful in the treatment of primary malignancies and metastases. The method is useful in inhibiting the growth of malignant cells, including, but not limited to malignant cells of gliomas, glioblastomas, oligodendrogliomas, astrocytomas, ependymomas, primitive neuroectodermal tumors, atypical meningiomas, malignant meningiomas, neuroblastomas, sarcomas, lymphomas, and carcinomas of all kinds, including hepatocarcinomas or adenocarcinomas.

Figure 1A:
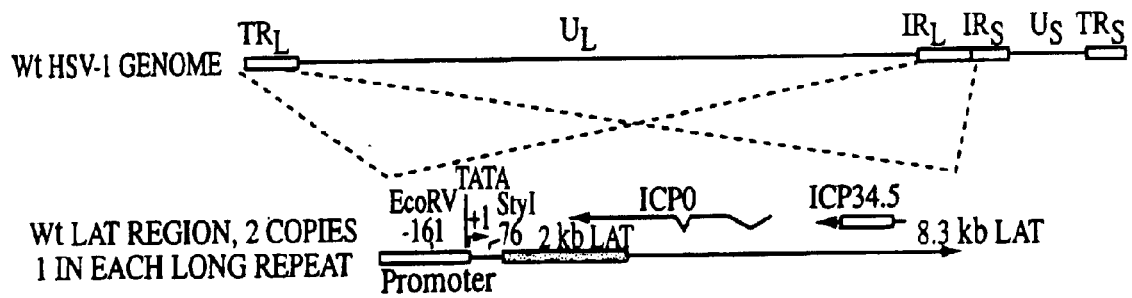
FIG. 1 shows a schematic of the structures of ΔLATΔ34.5 and PromΔLATΔ34.5-GFP compared to wild type HSV-1 genome.

In the inventive method, an HSV-1-derived viral vector containing in its DNA a deletion in both copies of the LAT gene and both copies of the ICP34.5 gene of HSV-1, is delivered to the malignant cell. Both of these genes are located in the viral long repeat of the wild type HSV-1 genome and therefore, in wild type HSV-1 virus both genes are present in two copies. (FIG. 1A). One of the advantages of using a combined LAT null mutant and γ34.5 null mutant HSV-1-derived vector, compared to LAT null mutants or γ34.5 null mutants, is that regardless of the infectious dose, the double mutant does not reactivate from latency. Transcripts encoding LAT gene product or ICP34.5 gene product are not detectably produced in a cell infected with the mutated virus. Thus, following the use of the method in inhibiting the growth of malignant cells in the brain or other tissue, or in delivery of foreign genes to malignant or non-malignant neurons or other cell types, there is no concern that spontaneous reactivation or virulence might occur at future times, with possible clinically harmful effects. Unlike wild type HSV-1, acute infection with a combined LAT-deletion/34.5-deletion mutant vector produces no corneal disease or other pathology.

Most preferably, the HSV-1-derived viral vector that is delivered to a malignant cell in accordance with the present method is a viral vector derived from HSV-1 strain McKrae. Strain McKrae is much more vigorous and virulent than other HSV-1 strains previously used as potential vectors, such as KOS, F, and 17syn+. It is an advantage of HSV-1-derived vectors derived from strain McKrae that they have the ability to efficiently kill cultured cells in vitro. This has not been demonstrated for other strains of HSV-1 virus.

Preferably, but not necessarily, the HSV-1-derived vector used in the method comprises a functional HSV thymidine kinase gene. When the HSV-1-derived viral vector is delivered to a malignant cell and internalized, the expressing host cell expresses transcripts encoding HSV thymidine kinase. The HSV thymidine kinase that is thereby produced in the expressing malignant cell can convert the drugs gancyclovir or acyclovir to a nucleotide analog within the malignant cell, inhibiting its growth. Thus, when an HSV-1-derived viral vector is employed that contains a functional HSV thymidine kinase gene, these drugs become particularly effective in treating malignancies.

The selectivity of the method lies in the replication conditional nature of the HSV-1-derived viral vector. HSV-1 can replicate and go into a lytic phase in actively growing cells, because the cell provides the metabolic background for HSV-replication. The HSV-1-derived vectors of the present invention are not selective in infecting cells. They infect non-malignant cells, such as normal neurons and glial cells just as well as they infect malignant cells, but they can only enter a lytic phase in rapidly growing malignant cells. Since the viral replication is conditional only in growing malignant cells, more of these malignant cells are preferentially inhibited, compared to the general population of less metabolically active non-malignant cells.

In another preferred embodiment of the method, the HSV-1-derived viral vector is an expression vector that further comprises at least one transcriptional unit of a LAT promoter sequence, or operative fragment thereof, operatively linked to a nucleic acid having a nucleotide sequence encoding a desired preselected protein, the presence of which polypeptide or protein results in toxicity to a malignant cell. A preferred example of a protein toxic to a malignant cell is human interferon-γ, or a functional fragment or fusion protein derived therefrom. When a malignant cell expresses a human interferon-γ gene from the LAT promoter sequence, the malignant cell constitutively produces higher levels of human interferon-γ, compared to homologous malignant cells not expressing the HSV-1-derived vector, which acts, like other cytokines, in a paracrine manner to produce a cytotoxic immnune response in the vicinity where the cytokine is secreted, thus preferentially inhibiting or killing other malignant cells close by in a tumor mass.

Other preferred polypeptides or proteins toxic to malignant cells include, but are not limited to, interleukin-2, interleukin-4, interleukin-6, interleukin-10, interleukin-12, granulocyte-macrophage colony stimulating factor, tumor necrosis factor-α, Fas ligand (e.g., of human or murine origin), human connexin-43, VP-16, VP-22, or functional fusion proteins derived from any of these.

Inhibition of the growth of malignant cells is determined by directly counting cells microscopically or by measuring physiologic or metabolic activity of malignant cells, in comparison with before-treatment values. For example, cell growth can be measured by evaluating the incorporation of [$^3$H]-thymidine into DNA during division or other known metabolic assessment techniques. Alternatively, inhibition of the growth of malignant cells is determined by measuring changes in the size of tumors comprising the malignant cells.

The present invention also relates to a method of expressing a gene encoding a preselected protein in a mammalian cell, whether a non-malignant or malignant cell. The method can be used to infect cells in vivo, i.e., within a mammal, or to infect cells grown in vitro. The method involves delivering to a mammalian cell an HSV-1-derived vector which contains a deletion in both copies of the LAT gene and both copies of the ICP34.5 gene of HSV-1, and contains at least one transcriptional unit of the constitutive LAT promoter sequence, or operative fragment thereof, operatively linked to a nucleic acid having a nucleotide sequence encoding any preselected protein, or operative fragment thereof. The protein can be one that is normally expressed by homologous uninfected cells, or, optionally, it can be a foreign protein. The cell expresses, from the LAT promoter, the nucleic acid encoding the desired preselected protein, in an elevated amount compared to uninfected homologous cells. Thus, the method can be used to deliver a foreign gene to "cure" a genetic defect.

Consequently, the present invention is also related to a method to treat a genetic defect in a mammal, i.e., a disease condition in a mammal that can be mitigated or ameliorated by expression of a specific exogenous gene, such as Alzheimer's disease, Multiple Sclerosis, Parkinson's disease, Gaucher's disease, or Huntingdon's disease in humans.

Many mammalian cell types have receptors for binding HSV-1, and binding of an HSV-1-derived vector results in the vector being internalized into the cell. However, for particular applications, internalizing of the HSV-1-derived vector is accomplished using any suitable method. Preferably, a bispecific antibody can be prepared to facilitate selective internalization of the HSV-derived vector into specific cell types. Such a bispecific antibody contains at least two covalently linked antibodies, one binding an HSV-1 specific epitope and another specifically binding an epitope specific for a particular cell type of interest. The bispecific antibody is first incubated with the HSV-derived vector before delivery, in order to allow the vector to preferentially infect a particular cell type.

The present invention also relates to a method of detecting the presence of a cell expressing HSV-1, which like the method of expressing a gene encoding a preselected protein in a mammalian cell, involves delivering to a mammalian cell an HSV-1-derived vector that contains a deletion in both copies of the LAT gene and both copies of the ICP34.5 gene of HSV-1, and contains at least one transcriptional unit of a LAT promoter sequence, or operative fragment thereof, operatively linked to a reporter gene, particularly, a nucleic acid having a nucleotide sequence encoding a fluorescent or light-emitting protein, or an operative fragment thereof.

Most preferably, the reporter gene, is a gene encoding Green Fluorescent Protein ([GFP]; or enhanced Green Fluorescent Protein [EGFP]), Yellow Fluorescent Protein, Blue Fluorescent Protein, a phycobiliprotein, such as phycoerythrin or phycocyanin, or any other protein which fluoresces under light of suitable wave-lengths of light. The HSV-expressing cell is then detected via fluorescence therefrom.

Another preferred reporter gene suitable for some applications is a gene encoding a protein that can enzymatically lead to the emission of light from a substrate(s); for purposes of the present invention, such a protein is a "light-emitting protein." For example, a light-emitting protein includes proteins such as luciferase or apoaequorin. The HSV-expressing cell is then detected via luminescence therefrom.

The cells are detected, sorted, isolated or selected from cells not expressing the HSV-1-derived expression vector with the aid of, for example, a flow-activated cell sorter (FACS) set at the appropriate wavelength(s). Alternatively, they are detected, isolated or selected manually from non-HSV-expressing cells using conventional microscopic technology.

For purposes of the present invention, "operatively linked" means that the promoter sequence, is located upstream from the coding sequence and that both sequences are oriented in a 5' to 3' manner with respect to each other, such that together they form a transcriptional unit from which transcription could take place in vitro in the presence of all essential enzymes, transcription factors, co-factors, activators, and reactants, under favorable physical conditions, e.g., suitable pH and temperature. This does not necessarily mean that, in any particular cell, conditions will favor transcription.

Delivering an HSV-1-derived vector to a mammalian cell can be by any suitable method. In some applications directed to malignant cells, the HSV-1-derived vector is preferably delivered by intratumoral injection through a surgical incision, for example, through a craniotomy for a brain tumor. Typically, surgical debulking of a tumor is done, if possible, before injection of the HSV-1-derived vector into the remaining tumor mass for infection of malignant cells.

Another preferred delivery method, useful for treating gliomatosis or carcinomatosis, is intrathecal injection of the vector. Another preferred delivery method is transvascular delivery, by intravenous or intra-arterial injection of HSV-1-derived viral particles.

For treating brain tumors, intra-arterial injection into the carotid artery is most preferred. It is preferable to facilitate passage of the vector across the blood-brain barrier. This can be accomplished, for example, by first disrupting the blood-brain barrier with a hypertonic (typically, 25%) mannitol infusion, immediately before or substantially simultaneously with the intra-arterial injection of HSV-1-derived vector. Alternatively, a vasoactive agent, such as bradykinin, or a functional analog, for example, RMP-7 (typically, about 1.5–3.0 µg/kg body weight over 10–15 minutes; Barnett et al. [1999]) is used to facilitate passage across the blood-brain barrier. Bradykinin and its analogs transiently and preferentially open the blood-tumor barrier in the neovasculature of brain tumors.

For treating a brain tumor, another preferred delivery method is stereotactic inoculation of the viral vector into the malignant tumor at a site having pre-established coordinates.

The foregoing are merely illustrative and not an exhaustive description of suitable methods for delivering the HSV-1-derived vector in accordance with the methods of the present invention.

The present invention also relates to an HSV-1-derived vector for use in any of the present methods. As described above, the HSV-1-derived vector contains in its DNA a deletion in both copies of the LAT gene and both copies of the ICP34.5 gene of HSV-1. A preferred vector is derived from HSV-1 strain McKrae.

Figure 1B:
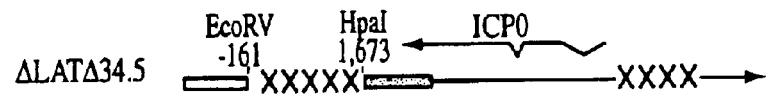

A preferred HSV-1-derived vector for use in the method is a viral vector designated ΔLATΔ34.5, or a derivative thereof. ΔLATΔ34.5 is derived from HSV-1 strain McKrae. The DNA structure of ΔLATΔ34.5 is shown in FIG. 1B; both copies of γ34.5 and LAT are deleted (FIG. 1B). The deletions include the promoters for both genes, the entire γ34.5 structural gene, and the first 1.67 kb of the structural region of LAT. This region of LAT contains the LAT function that results in enhanced spontaneous reactivation. ΔLATΔ34.5 contains a fully functional HSV thymidine kinase gene. The ΔLATΔ34.5 vector replicates preferentially in malignant cells and selectively kills or inhibits the growth of malignant cells.

The construction of ΔLATΔ34.5 is illustrated in FIG. 1. The top of the figure shows the prototypic organization of the wild type HSV-1 genome. The $TR_L$ (terminal repeat long) and the $IR_L$ (internal or inverted repeat long) each contain identical copies of the LAT region, including the gene for ICP34.5 that overlaps a portion of the LAT gene in the opposite orientation.

FIG. 1A shows a blow up of the LAT region, identical in both long repeats. The primary LAT transcript is 8.3 kb long. The solid rectangle represents a very stable portion of the LAT transcript called the 2 kb LAT. The open rectangle indicates the location of the LAT promoter. TATA indicates the LAT TATA-box within the promoter. The small arrow (at +1) indicates the start of LAT transcription. EcoRV, StyI, and HpaI are restriction sites that define boundaries of deleted areas shown below. The relative size and location of ICP34.5 is shown above LAT. The open rectangle indicates the ICP34.5 open reading frame. The location of ICP0 is shown for reference.

FIG. 1B shows ΔLATΔ34.5, containing 2 deletions in the LAT region. The first deletion extends from the EcoRV restriction site at LAT nucleotide −161 to the HpaI restriction site at LAT nucleotide 1,673. This deletion removes the core LAT promoter and the first 1.67 kb of the LAT transcript. The second deletion encompasses the region corresponding to LAT nucleotides 6.2–7.1 kb and thus all of the gene for ICP34.5. Both copies of the LAT/ICP34.5 region (1 in each long repeat) are identical. ΔLATΔ34.5 therefore makes no LAT RNA transcripts and no ICP34.5 RNA transcripts.

Figure 1C:
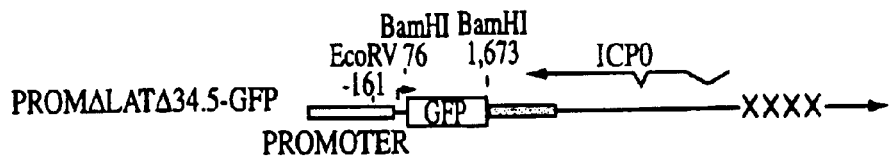
Figure 2:
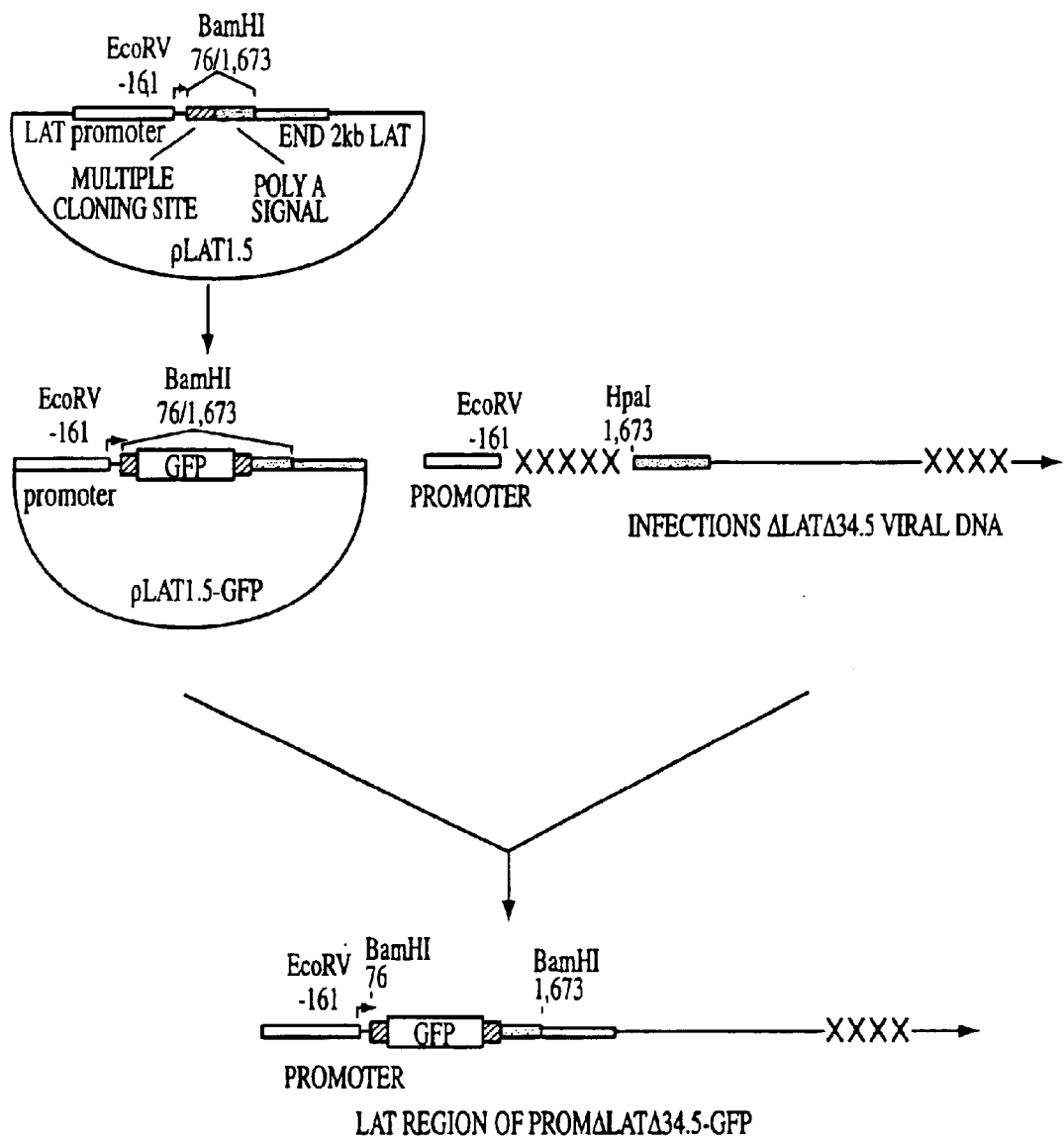
FIG. 2 illustrates the construction of PromΔLATΔ34.5-GFP.

Another preferred example of the HSV-1-derived vector of the present invention is a viral vector designated PromΔLATΔ34.5 (FIG. 1C), or a derivative thereof. PromΔLATΔ34.5 is derived from HSV-1 strain McKrae, and is particularly derived from ΔLATΔ34.5, sharing its ability to selectively kill or inhibit the growth of malignant cells. Like ΔLATΔ34.5, PromΔLATΔ34.5 is a LAT null mutant and a γ34.5 null mutant, also having a functional HSV thymidine kinase gene. It contains a DNA having the LAT promoter, a BamHI site cloning site into which foreign (xenogeneic) genes, i.e., genes not naturally expressed from the LAT promoter, such as those encoding GFP or human interferon-γ, can be inserted. PromΔLATΔ34.5 also has a Poly A signal site. (FIGS. 1 and 2). This vector is capable of long term high level expression of any foreign (xenogeneic) or exogenous gene in neurons or other cells.

In PromΔLATΔ34.5, the region of the LAT promoter from the EcoRV site to the start of the LAT transcript and the region of LAT from the start of LAT transcription to the StyI site at nucleotide 76 have been restored to ΔLATΔ34.5. The original StyI site at LAT nucleotide 76 and the end of the original deletion at the HpaI site at LAT nucleotide 1673 have been replaced by a single unique BamHI site into which a xenogeneic gene can be inserted and expressed under the transcriptional control of the LAT promoter.

The construction of PromΔLATΔ34.5 is further illustrated in FIG. 2. The plasmid pLAT1.5 was constructed; pLAT1.5 contains the LAT promoter from LAT nucleotides −799 to +76 (i.e., the first 76 nucleotides of the LAT transcript), followed by a small multiple cloning site, a Poly A signal site, a unique BamHI site, and LAT nucleotides 1,673 to 4,656. The foreign gene GFP was cloned into the multiple cloning site to produce pLAT1.5-GFP, but any other foreign gene encoding a preselected protein can be cloned into the multiple cloning site instead. Cells were co-infected with pLAT1.5-GFP and ΔLATΔ34.5 infectious DNA to produce PromΔLATΔ34.5-GFP by homologous recombination. The structure of the LAT region in the DNA of PromΔLATΔ34.5-GFP is thus as follows. The LAT promoter (including all upstream sequences) up to LAT nucleotide 76, followed by a foreign gene (GFP), followed by a Poly A site, followed by the remainder of LAT starting at LAT nucleotide 1,673. The region of LAT from 77 to 1,672 is therefore deleted and no LAT can be made. The genomic location containing the gene for ICP34.5 (and therefore the corresponding of region of LAT from 6.2–7.1 kb) is also deleted.

PromΔLATΔ34.5 can contain any foreign gene. The foreign gene is inserted into the cloning site of plasmid vector pLAT1.5. In FIG. 2, GFP is used as an illustrative example of such a foreign gene. The foreign gene can then be inserted into ΔLATΔ34.5 by homologous recombination of genomic ΔLATΔ34.5 DNA with the pLAT 1.5 plasmid vector DNA containing the foreign gene, as shown in FIG. 2 for the foreign gene GFP. In the final HSV-1-derived vector (in this case PromΔLATΔ34.5-GFP), the foreign gene is under the control of the LAT promoter and is followed by a Poly A site. The LAT promoter is highly active in a wide variety of cell types, and particularly in neurons, producing long term expression of the foreign gene, even after the virus has become latent. This is a significant improvement over HSV-1 vectors using other viral promoters, since these other promoters are unlikely to provide long term expression.

The present invention also relates to a mammalian cell containing an HSV-1-derived vector of the present invention, or unpackaged (unencapsidated) DNA thereof. The mammalian cell is a malignant cell or a non-malignant cell, originating in any mammalian species, but preferably derived from or contained in a human, non-human primate, mouse, rat, gerbil, hamster, or rabbit. The cell is grown in vitro or is situated in vivo. A preferred malignant cell of the present invention is derived from or is contained in a glioma, glioblastoma, oligodendroglioma, astrocytoma, ependymoma, primitive neuroectodermal tumor, atypical meningioma, malignant meningioma, neuroblastoma, sarcoma, lymphoma, or carcinoma. Examples of preferred non-malignant cell include neuronal, epidermal, osteogenic, lymphatic, endothelial, epithelial, hepatic, breast, ovarian, uterine, or prostate cells, but a cell derived from any other kind of mammalian tissue is also preferred.

The present invention also relates to a kit for expressing in a mammalian cell a gene encoding a preselected protein. The kit is a ready assemblage of materials for facilitating the practice of the present method or use of the present HSV-1-derived vector to infect a mammalian cell. A kit of the present invention contains at least an HSV-1-derived vector of the present invention and instructions for its effective use. The materials or components assembled in the kit are provided to the practitioner stored in any convenient and suitable way that preserves their operability and utility. For example the components can be in dissolved, dehydrated, or lyophilized form; they can be provided at room, refrigerated or frozen temperatures.

The present invention provides LAT null/ICP34.5 null HSV-1-derived vectors that are non-virulent and are not spontaneously reactivated. These vectors are safer and more effective than previously available HSV-derived vectors for the treatment of malignancies, and are particularly useful in the treatment of brain tumors in vivo. In addition, the HSV-1-derived vector of the present invention is able to inhibit the growth of malignant cells in in vitro culture.

The foregoing descriptions of the methods, vectors, cells and kits of the present invention are illustrative and by no means exhaustive. The invention will now be described in greater detail by reference to the following non-limiting examples.

EXAMPLES

Example 1

Culture of Cells and HSV-1

Two kinds of human glioblastoma multiforme (GBM) primary cells were isolated from two different surgically obtained GBM specimens. The human glioblastoma cell line U87 MG, normal neuron HCN-1A cells, and human umbilical endothelial cells (HUVEC) were purchased from American Type Culture Collection (Rockville, Md.). Normal human astrocyte HFA cells were kindly provided by Carlo Tornatore (Laboratory of Molecular Medicine and Neuroscience, National Institute of Neurological Disorder and Stroke, Bethesda, Md.). All cells except HCN-1A and RS cells were grown in Ham's F12/DME containing 10% fetal bovine serum and antibiotics. HCN-1A and rabbit skin (RS) cells were cultured in Dulbecco's minimum essential medium supplemented with 10% fetal bovine serum and antibiotics. Aseptic technique was used in maintaining all cell cultures. HSV-1 strain McKrae (wild type) and all HSV-1-derived expression vectors were routinely stored in tissue culture medium at −70° C. until use.

Example 2

Figure 3A:
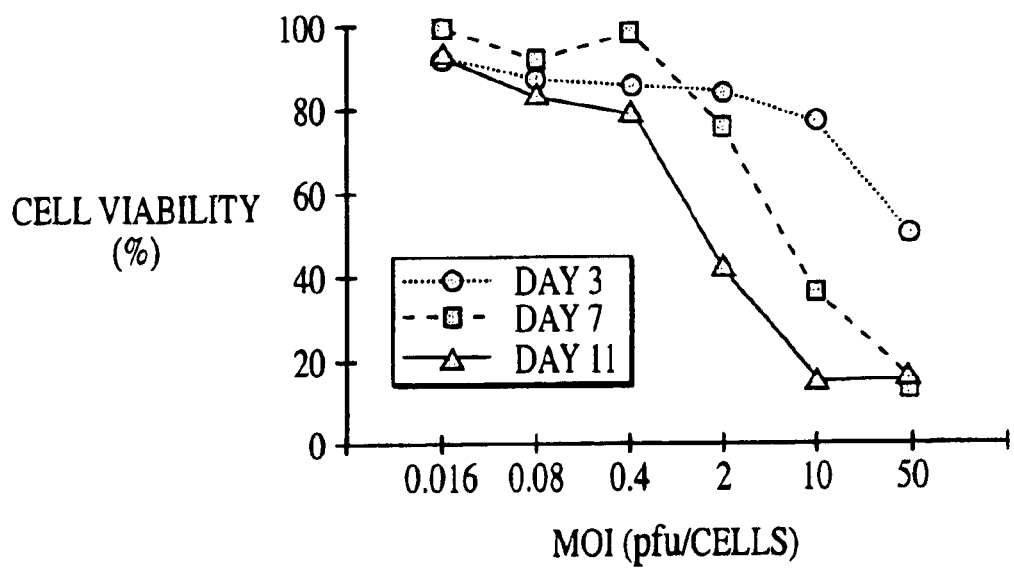
FIG. 3 illustrates cytotoxicity of PromΔLATΔ34.5-GFP in human U-87 MG glioma cells (FIG. 3A) and human glioblastoma multiforme primary cells (GBM-1.
FIG. 3B, GBM-2.
FIG. 3C).
Figure 3B:
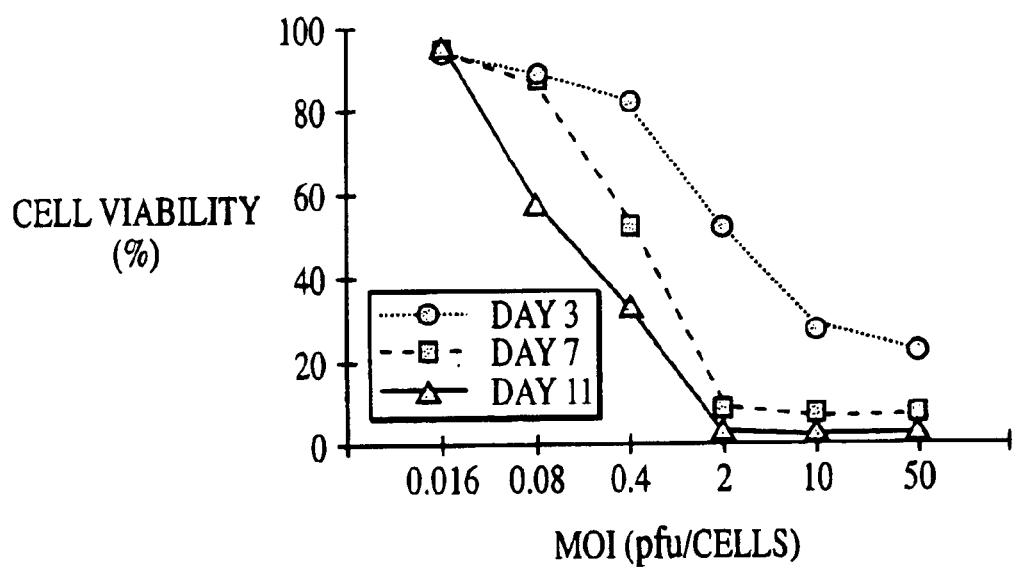
Figure 3C:
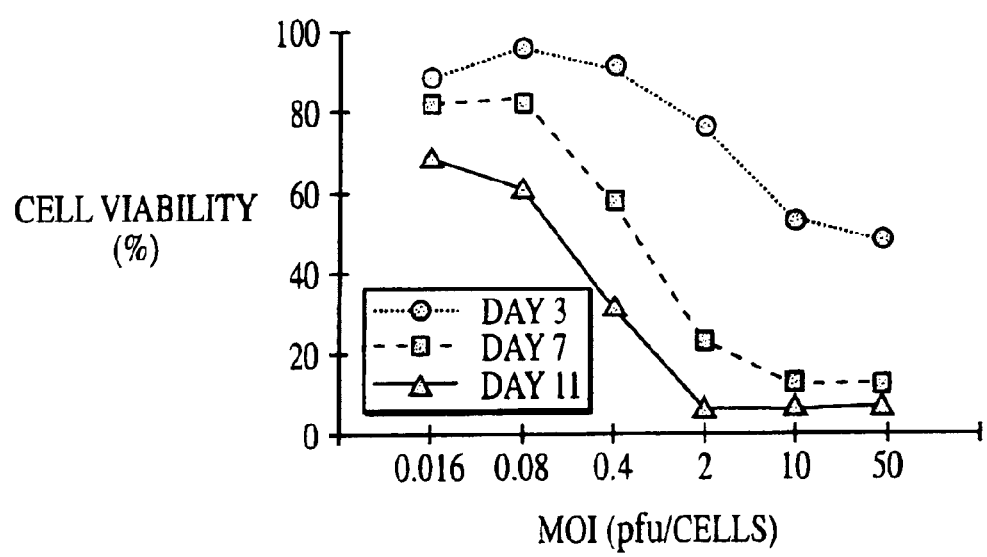

Determination of Cytotoxicity in In Vitro Cell Culture $1 \times 10^3$ cells of U 87MG or of the two GBM primary cell lines (GBM-1 and GBM-2) were seeded separately in each well of 96-well plates. Twenty four hours after seeding, PromΔLATΔ34.5-GFP was delivered to these cells at various titers. Three, seven and eleven days after infection with this viral vector, cell viability was determined using cell proliferation reagent WST-1 (Boehringer Mannheim, Indianapolis, Ind.), which indicates the overall activity of mitochondrial dehydrogenases, and by measuring the absorbance of the dye solution in each well with a multi-well spectrophotometer. Viability of cells in the absence of PromΔLATΔ34.5-GFP represented 100% viability. As shown in FIG. 3, the viable numbers of all three kinds of cells decreased with time in a dose-dependent manner in response to exposure to PromΔLATΔ34.5-GFP.

Example 3

In Vitro Cellular Expression of Green Fluorescent Protein (GFP) from PromΔLATΔ34.5-GFP To detect GFP expression from the LAT promoter, U 87MG and the two GBM primary cell lines (GBM-1 and GBM-2) were separately seeded in 4-well chamber slides ($2 \times 10^4$ cells/well). Twenty-four hours after seeding, PromΔLATΔ34.5-GFP was delivered at a MOI of 0.1 pfu/cells. On days 1, 2, 3 and 5, cells were fixed with 4% paraformaldehyde in PBS for 30 min, washed, mounted and examined with fluorescence microscopy using a filter for GFP fluorescence.

Figure 4A:
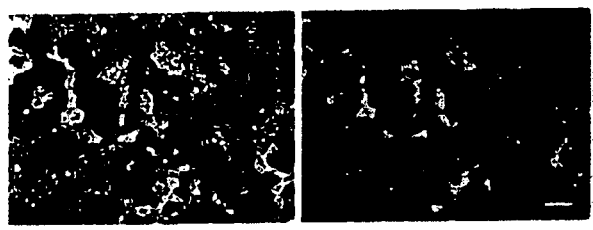
FIG. 4 shows human U-87 MG glioma cells (FIG. 4A) and human glioblastoma multiforme primary cells (GBM-1.
FIG. 4B, GBM-2.
FIG. 4C), under phase contrast (left panels) and with fluorescent microscopy showing fluorescence secondary to expression of green fluorescent protein from PromΔLATΔ34.5-GFP (right panels).
Figure 4B:
Figure 4C:

Cellular expression of GFP after 3 days is shown in the left-hand panels of the micrographs in FIG. 4. The right-hand panels show the same cells under phase contrast. In U87 MG cells, GFP-positive cells were barely detectable on day 1 post-infection. They showed GFP positivity and widespread cytopathic effects on day 3. (FIG. 4A). On day 5, almost all cells expressed GFP and a considerable number of cells had died and/or sloughed from the plate surface. In GBM-1, GFP-positivity was observed in a few cells on day 1 post-infection. On day 3, the vast majority of the cells were positive for GFP and exhibited cytopathic effects. (FIG. 4B). By day 5, almost all cells were dead and/or sloughed from the plate surface. GBM-2 cells behaved in a manner similar to GBM-1. (FIG. 4C).

Example 4
Determinations of Infectivity

To determine infectivities of wild type HSV-1 (strain McKrae) or PromΔLATΔ34.5-GFP with respect to non-malignant cells, neuronal (HCN-1A), astrocyte (HFA) and endothelial cells (HUVEC), were separately seeded in 24-well plates ($2 \times 10^4$ cells per well). Twenty four hours after seeding, HCN-1A, HFA or HUVEC cells were infected with HSV-1 wild type strain McKrae or PromΔLATΔ34.5-GFP at a MOI of 0.1 pfu/cells. The cells were examined with a phase contrast microscope on days 3, 5 and 7. In each assay, controls were mock-infected.

Figures 5A, 5B, 5C:
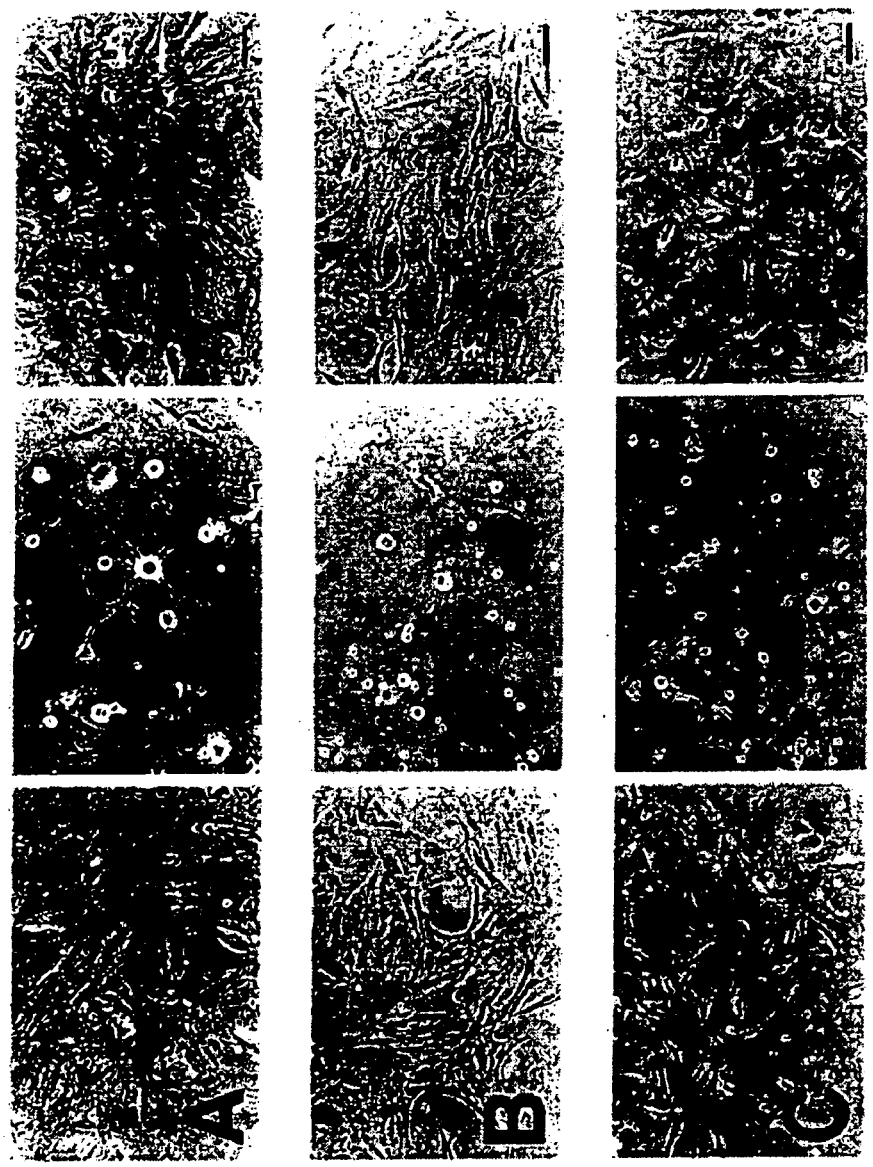
FIG. 5 shows non-malignant human normal neuronal HCN-1A cells (FIG. 5A), astrocyte HFA cells (FIG. 5B) and endothelial HUVEC cells (FIG. 5C) infected with wild type HSV-1 (center panels) or with PromΔLATΔ34.5-GFP (right panels) at a MOI of 0.1 pfu/cells. Control cells were mock-infected (left panels). Bar length is 100 μm.

Micrographs taken on day 3 are shown in FIG. 5. On day 3, the majority of HCN-1A cells infected with wild type HSV-1 revealed morphological changes such as neuronal differentiation. (FIG. 5A, center panel). Virtually all HCN-1A cells infected with PromΔLATΔ34.5-GFP remained normal (FIG. 5A, right panel). By day 5, all wild type HSV-1-infected HCN-1A cells had been killed. In contrast, only about a half of the cells infected with PromΔLATΔ34.5-GFP demonstrated a slight morphological change.

Virtually all HFA cells infected with wild type HSV-1 were killed by day 3 (FIG. 5B, center panel), but HFA cells infected with PromΔLATΔ34.5-GFP showed few morphological changes. (FIG. 5B, right panel). On day 5, only a few HFA cells infected with PromΔLATΔ34.5-GFP showed any morphological change. HUVEC cells behaved in a manner similar to HFA cells. On day 3, about 90% of HUVEC infected with wild type HSV-1 were killed (FIG. 5C, center panel), but all HUVEC cells infected with PromΔLATΔ34.5-GFP were normal. (FIG. 5C, right panel). By day 5, there were no viable HUVEC cells infected with wild type HSV-1. Cells infected with PromΔLATΔ34.5-GFP were all viable, but in some HUVEC cells a foamy structure appeared in the nucleus. Mock-infected control cells of each of the three cell lines showed no morphological changes. (FIGS. 5A-C, left panels).

Example 5
In Vitro Sensitivity to Drug Treatment with Gancyclovir

Confluent monolayers of RS cells in 6-well plates were infected with 100 pfu of wild type HSV-1 or infected with PromΔLATΔ34.5-GFP in 500 μl of tissue culture medium for a 1-hour incubation period at 37° C. After the viral inoculum was removed, minimal essential medium (MEM) containing 5% fetal bovine serum, 1% methylcellulose and various concentrations of gancyclovir, were added to triplicate cultures and cells were incubated at 37° C. for 3 days. Plaques were visualized by Giemsa stain and were counted.

Figure 6:
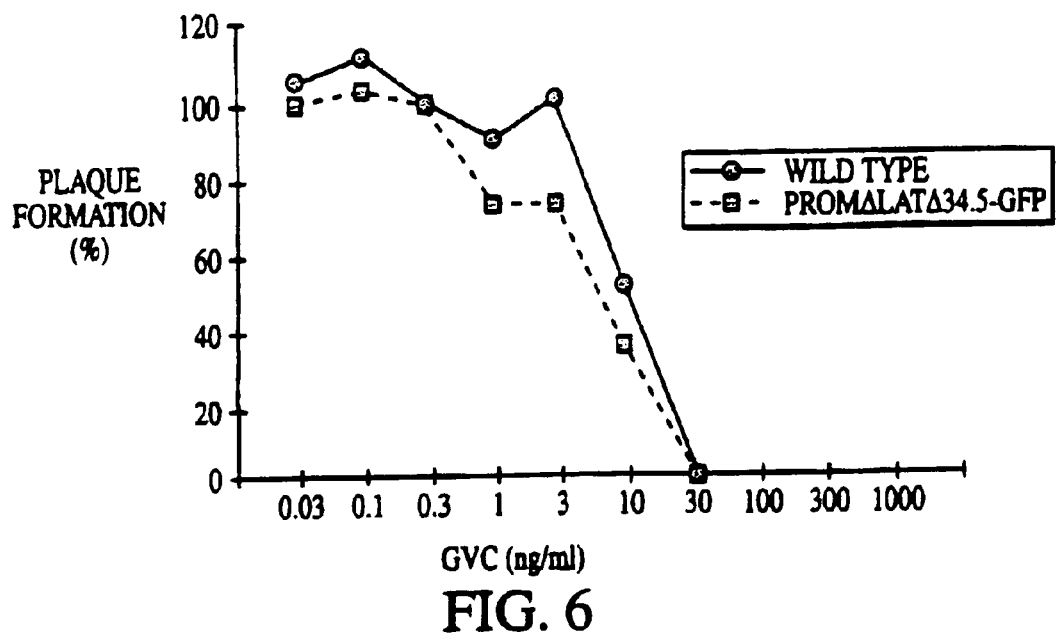
FIG. 6 shows plaque formation as dose-dependent with respect to gancyclovir concentration in confluent monolayers of rabbit skin (RS) cells infected with 100 pfu of wild type HSV-1 or with PromΔLATΔ34.5-GFP.

FIG. 6 shows gancyclovir sensitivities in RS cells hosting either wild type HSV-1 or PromΔLATΔ34.5-GFP. Plaque reduction assays demonstrated that cells infected with PromΔLATΔ34.5-GFP are as sensitive or more sensitive to gancyclovir, compared to cells infected with wild type HSV-1. (FIG. 6). The numbers of plaques in the wells without gancyclovir represents 100%.

Example 6
PromΔLATΔ34.5-GFP in Mammalian Cells In Vivo
Mammals.

Six-week-old female mice (BALB/c) or nude mice (BALB/c-nu/nu) were used for all animal experiments and were obtained from Charles River (Wilmington, Mass.).
Safety of PromΔLATΔ34.5-GFP In Vivo.

To confirm the non-neurovirulence of PromΔLATΔ34.5-GFP, 18 mice (BALB/c) were stereotactically inoculated with 5 μl of sterile culture medium containing either PromΔLATΔ34.5-GFP or wild type HSV-1. Mice were equally divided into 3 groups; Group A mice received $2 \times 10^5$ pfu wild type HSV-1; Group B mice received $2 \times 10^5$ pfu PromΔLATΔ34.5-GFP; and Group C received $1 \times 10^7$ pfu PromΔLATΔ34.5-GFP. Mice were followed for 60 days post-inoculation.

All 6 mice in Group A died within 6 days after infection. All 6 mice in Group B, inoculated with PromΔLATΔ34.5-GFP, were alive after 60 days. One mouse out of the six in Group C, died on day 9 post-inoculation.
Survival of Mammals with Malignancies after Delivery of PromΔLATΔ34.5-GFP and Responses to Gancyclovir Treatment.

Survival studies were carried out to determine the efficacy of treatment with the present method of inhibiting the growth of a malignant cell. Animals were monitored and when they met criteria, they were euthanised. Criteria included moribund state, inability to feed, cachexia, and inability to support weight or to ambulate. If animals survived over 3 months, they were euthanised (via $CO_2$ asphyxiation) and their brains were harvested for histology. For surgical procedures, all mice were anesthetized with an intraperitoneal injection of ketamine (100 mg/kg) and xylazine (10 mg/kg).

U87MG cells ($2 \times 10^5$) were stereotactically implanted in the right basal ganglia of 30 nude mice. After anesthesia, a linear skin incision was made on the midline of the skull. A burr hole was made on the coronal suture approximately 2 mm lateral to the midline on the right side. After the mice were immobilized in a stereotactic apparatus, $2 \times 10^5$ U87 MG cells in 2 μl of Ham's F12/DME medium, containing 1.2% methylcellulose, were injected with a Hamilton syringe to a depth of 2 mm from the cortical surface over a period of 2 min. Before retracting, the needle was left as it was for 2 additional min. The skin incision was closed using sterile surgical staples. Thereafter, animals were divided into 3 groups of ten mice each.

Seven days after tumor cells were implanted, the first group of mice received stereotactic inoculation of $4.4 \times 10^6$ pfu of PromΔLATΔ34.5-GFP in 2 μl of MEM/FBS/antibiotics medium at the same location as the tumor implantation. This was followed by regular intraperitoneal injections of gancyclovir (7.5 mg/kg every 12 hr), started 7 days after inoculation with PromΔLATΔ34.5-GFP, and continued for an additional 7 days.

The second group of mice received the same treatment as the first group, except that intraperitoneal injections of saline were administered instead of gancyclovir.

The third group (control) of mice received a stereotactic inoculation containing only sterile cell culture medium in the tumor site, followed by a series of intraperitoneal injections of saline as in the second group.

The survival of these animals was followed until day 100 post-implantation.

In parallel time course experiments done for histopathological analysis, animals in each group were sampled and euthanised at days 10, 14, 21, and 28 post-implantation. Brains were removed, the tumors were dissected out aseptically in a dissection hood, and frozen on dry ice, and frozen sections were sectioned to 10 µm thickness in a cryostat. The sections were used for detection of GFP expression or for staining with hematoxylin & eosin (HE). To determine the expression of GFP, these sections were fixed with 4% paraformaldehyde/PBS for 5 min, then washed with phosphate buffered saline. Sections were mounted with Immuno-Fluore Mounting Medium (ICN Biomedicals, Inc., Aurora, Ohio) and examined by fluorescence microscopy.

Figure 7:
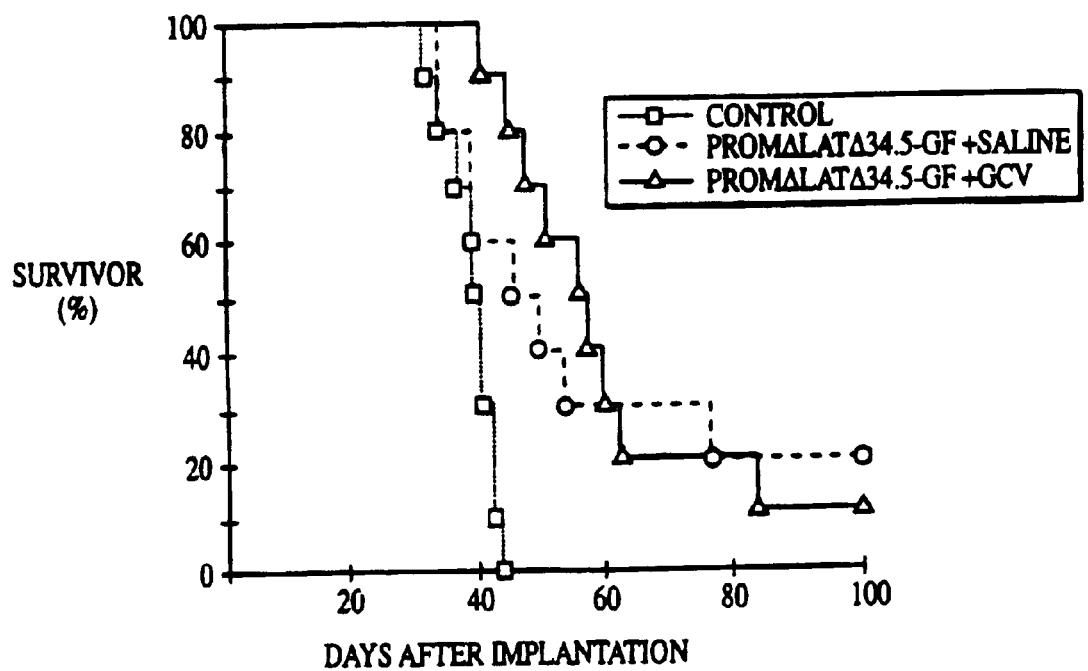
FIG. 7 shows a Kaplan-Meier survival analysis for nude mice with brain tumors treated with intratumoral injection of PromΔLATΔ34.5-GFP with or without subsequent treatment with gancyclovir (GCV).

A Kaplan-Meier survival curve summarizes the results in FIG. 7. All mice in the control group died within 33 to 44 days post-implantation. One of 10 mice (10%) in the first group receiving PromΔLATΔ34.5-GFP and gancylovir treatment survived at least 100 days after tumor implantation. In the second group, receiving PromΔLATΔ34.5-GFP without gancylovir treatment, 2 of 10 mice (20%) survived 100 days after implantation. Statistical analysis revealed that the differences of survival time between the control group and either of the PromΔLATΔ34.5-GFP treatment groups (i.e., +/− gancyclovir treatment) were statistically significant ($p=0.0191$ and $p<0.0001$ respectively). However, in this experiment there was no significant difference in survival time between the treatment group receiving gancyclovir and the treatment group not receiving gancyclovir.

Figure 8A:
FIG. 8 shows brain sections from nude mice that were stereotactically implanted with malignant U-87 MG cells (FIGS. 8A–E). and were later inoculated intratumorally with PromΔLATΔ34.5-GFP (FIGS. 8B–E) and treated with gancyclovir (FIG. 8E only), or of controls (FIG. 8A). Bar length is 50 μm.

Tumors from mice in either the first or second treatment groups were relatively small in size and irregularly shaped, compared with tumors in the control group. Tumors in the control group became enlarged with time and were round, containing cells possessing high cellularity and pleomorphism. FIG. 8 shows HE-stained sections (left panels) and GFP expression, as detected by fluorescence microscopy (right panels). On day 10 post-implantation, HE-stained sections of malignant tumor tissue from the right basal ganglia of mice in the control group is shown in FIG. 8A (left panel);control tissue lacked GFP positivity. (FIG. 8A, right panel).

Figure 8B:

HE-staining of tumor tissue from mice in the second treatment group, sampled at day 10 post-implantation (i.e., day 3 post-viral inoculation), revealed necrotic tumor tissue with infiltration of inflammatory cells (FIG. 8B, left).

Figure 8C:
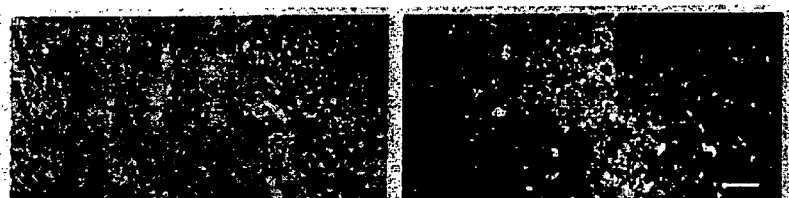
Figure 8D:
Figure 8E:
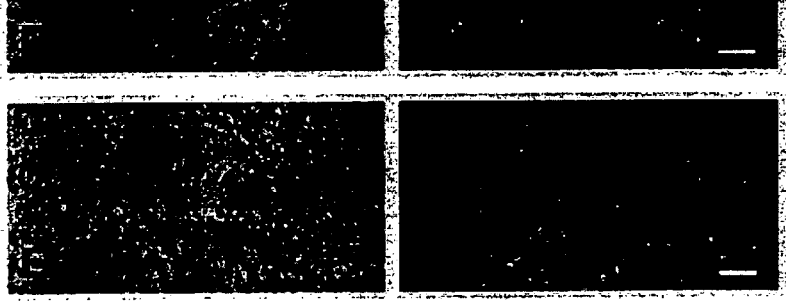

On day 14, post-implantation (day 7 post-viral inoculation), tumor tissue sections exhibited necrotic and cell-lytic features. (FIG. 8C, left). On day 21 (14 days post viral inoculation; FIG. 8D, left) or day 28 (21 days post-viral inoculation; data not shown), tumor tissues resembled sections from day 14, and tumor tissue sampled from the first treatment group (+gancyclovir), on Day 21, had the same features. (FIG. 8E, left) All sections of tumors from both treatment groups showed GFP positivities. (FIGS. 8B-D, right).

Figure 9A:
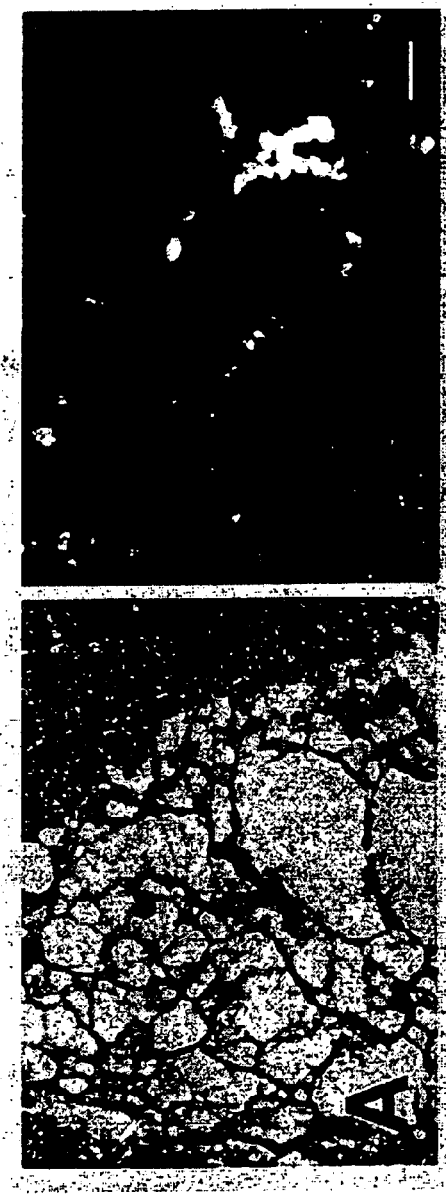
FIG. 9 shows histological sections of malignant U-87 MG cells from 100-day survivor mice treated with PromΔLATΔ34.5-GFP, with subsequent gancyclovir treatment (FIG. 9B) or without gancyclovir treatment. Left panels are HE stained slides; right panels are slides viewed with fluorescence microscopy to show fluorescence secondary to expression by cells of green fluorescent protein from PromΔLATΔ34.5-GFP. Bar length is 50 μm.

On day 100, all remaining 3 survivors were euthanised and their brains were removed for histological analysis as described above. In the brain of a survivor treated with PromΔLATΔ34.5-GFP followed by intraperitoneal saline injections, HE-stained sections showed numerous cavities in the tumor tissue accompanied by necrosis. (FIG. 9A, left panel). Tumor cells had GFP positivities. (FIG. 9A, right panel)

Figure 9B:
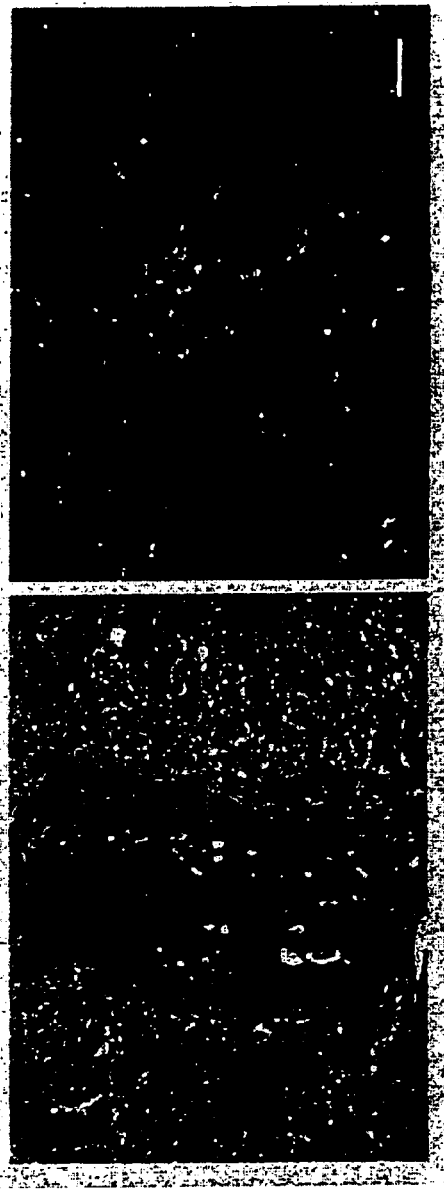

In the surviving mouse that received PromΔLATΔ34.5-GFP and gancyclovir injections, tumors were relatively small in size considering the survival date of 100 days. Tumor tissue appeared necrotic or cell-lytic and was surrounded by a gliosis. (FIG. 9B, left panel). The tumor cells were positive for GFP expression. (FIG. 9B, right panel).

The foregoing examples being illustrative but not an exhaustive description of the embodiments of the present invention, the following claims are presented.

We claim:

1. A kit for expressing in a mammalian cell a gene encoding a preselected protein, containing an HSV-1-derived vector selected from the group consisting of PromΔLATΔ34.5 and PromΔLATΔ34.5-GFP, or containing a derivative of any of these.

2. An HSV-1-derived vector selected from the group consisting of PromΔLATΔ34.5, a derivative of PromΔLATΔ34.5, PromΔLATΔ34.5-GFP, and a derivative of PromΔLATΔ34.5-GFP.

3. The HSV-1-derived vector of claim 2, further comprising a functional HSV thymidine kinase gene.

4. The HSV-derived vector of claim 2, wherein said HSV-1-derived vector is derived from HSV-1 strain McKrae.

* * * * *